United States Patent [19]

Sticklen et al.

[11] Patent Number: 5,539,095

[45] Date of Patent: Jul. 23, 1996

[54] CHITINASE CDNA CLONE FROM A DISEASE RESISTANT AMERICAN ELM TREE

[75] Inventors: Masomeh B. Sticklen, Okemos; Ravindra K. Hajela, Holt, both of Mich.

[73] Assignee: Board of Trustees operating Michigan State University, East Lansing, Mich.

[21] Appl. No.: 286,020

[22] Filed: Aug. 4, 1994

[51] Int. Cl.$^6$ .............................. C12N 9/24; C12N 15/29; C12N 15/56; C12N 15/82

[52] U.S. Cl. ................ 536/23.6; 536/23.2; 435/69.1; 435/70.1; 435/71.1; 435/172.3; 435/200; 435/240.4; 435/252.33; 435/69.8

[58] Field of Search ..................... 536/23.2, 23.6; 435/69.1, 70.1, 71.1, 172.3, 200, 240.4, 252.33, 69.8

[56] References Cited

FOREIGN PATENT DOCUMENTS 9007001  6/1990  WIPO ........................... C12N 15/56

OTHER PUBLICATIONS

Meins, F., Ahl, P., Plant Cell 61:155–161 (1989).
Metraux, J. P., et al., Physiol Mol Plant Path 28:161–169 (1986).
Rasmussen, U., et al., Planta 187:328–334 (1992).
Roby, D., et al., Plant Sci 52:175–185 (1987).
Roby, D., et al., Molecular Plant Pathology 33:409–417 (1988).
Kurosaki, F., et al., Physiol Mol. Plant Path 31:211–216 (1987).
Roby, D., et al., Biochem Biophys. Res. Comm. 143(3):885–892 (1987).
Boller, T., Oxford Surveys of Plant Molecular and Cell Biology 5:145–174 (1988).
Boller, T., et al., Planta 157:22–31 (1983).
Parsons, T. J., et al., Proc. Natl. Acad Sci USA 86:7895–7899 (1989).
Broglie, et al., Proc. Natl. Acad, Sci USA 83:6820–6824 (1986).
Shinshi, H., et al., Plant Mol. Biol. 14:357–368 (1990).
von Heijne, G., Eur. J. Biochem 133:17–21 (1983).
Chrispeels and Raikhel, The Plant Cell vol. 3 1–9 (1991).
Joshi, C. P., Nucleic Acids Research, vol. 15 No. 23, 9627–9640 (1987).
von Heijne, G., Sequence analysis in molecular biology: Treasure trove or trivial pursuit Academic Press, Inc. San Diego (1987).
Hopp and Woods, Proc. Natl Acad Sci USA 78(6):3824–3828 (1981).
Kyte and Doolittle, J. Mol. Biol 157:105–132 (1982).
Karlin, S. and Altschul, S. F. (1990) Methods for assessing the statistical significance of molecular sequence features by . . . Proc. Natl Acad. Sci. USA 87:2264–226
Sticklen et al., Dutch Elm Disease Research pp. 1–5, 1994 Springer–Verlag, New York, NY.
J. L. Sherald, et al., Canadian Journal of Forest Research, vol. 24, No. 4, 647–653 (1994).
Sticklen et al. 1991. Phytoprotection 72(1):1–13.

Primary Examiner—David T. Fox
Attorney, Agent, or Firm—Ian C. McLeod

[57] ABSTRACT cDNA as set forth in SEQ ID NO:1 encoding a chitinase, a signal peptide and a vacuole sorting peptide. The chitinase is antifungal and can be used to treat plants, particularly American elms infected with a fungus which kills the trees. The cDNA can be used to produce recombinant cells which produce the chitinase or which impart resistance to the fungi.

4 Claims, 5 Drawing Sheets

CGGGATTAACGAGATTCCCACTGTCCCTGTCTACTACCCAGCGAAACCACAGCCAAGGGA

ACGGGCTTGGCAGAATCAGAACTAAACATGAGGTTTTGGGCATTGACGACACTTTCTCTT
                              MetArgPheTrpAlaLeuThrThrLeuSerLeu

CTATTGTCCATTATCCAAGGAGGCTGGGCAGAGCAATGTGGAAGCCAAGCTGGGGGTGCA
LeuLeuSerIleIleGlnGlyGlyTrpAlaGluGlnCysGlySerGlnAlaGlyGlyAla

GTGTGTCCCGTTGGGCTCTGCTGCAGCAAATTTGGGTGGTGTGGGAGCACAAACGAGTAC
ValCysProValGlyLeuCysCysSerLysPheGlyTrpCysGlySerThrAsnGluTyr

TGTGGTGATGGCTGCCAAAGCCAATGTGGCGGCAGCGGTAGCGATGACATTGGCGGTCTC
CysGlyAspGlyCysGlnSerGlnCysGlyGlySerGlySerAspAspIleGlyGlyLeu

ATATCAAGCTCCGCCTTTAATGACATGCTTAAGCATCGTAACGACGGTGGTTGTCCTGCC
IleSerSerSerAlaPheAsnAspMetLeuLysHisArgAsnAspGlyGlyCysProAla

AAGGGGTTTTACACCTATGATGCTTTTATTGCGGCTGCCAAGGCTTTCCCTGCATTTGGC
LysGlyPheTyrThrTyrAspAlaPheIleAlaAlaAlaLysAlaPheProAlaPheGly

TCCACCGGCGATGATACCACCCGTAAAAGGGAGATTGCTGCTTTCTTAGGTCAAACTTCC
SerThrGlyAspAspThrThrArgLysArgGluIleAlaAlaPheLeuGlyGlnThrSer

CATGAAACTACAGGTGGGTGGGCAAGTGCACCCGACGGTCCATACTCTTGGGGATACTGC
HisGluThrThrGlyGlyTrpAlaSerAlaProAspGlyProTyrSerTrpGlyTyrCys

TACAATAGGGAGCAAAACCCTTCTTCCGATTATTGTTCTTTTAGTCCTACTTGGCCTTGT
TyrAsnArgGluGlnAsnProSerSerAspTyrCysSerPheSerProThrTrpProCys

GCTTCCGGAAAGAGATACTTTGGCCGTGGTCCCATTCAACTCTCCTGGAACTACAACTAT
AlaSerGlyLysArgTyrPheGlyArgGlyProIleGlnLeuSerTrpAsnTyrAsnTyr

GGACAGTGTGGAAGGGCCATAGGAGCAAACCTATTAAACAACCCTGATCTCGTAGCAACT
GlyGlnCysGlyArgAlaIleGlyAlaAsnLeuLeuAsnAsnProAspLeuValAlaThr

GACCCTGTCATTTCCTTCAAAACGGCCTTATGGTTCTGGATGACCCCACAGTCACCAAAG
AspProValIleSerPheLysThrAlaLeuTrpPheTrpMetThrProGlnSerProLys

CCCTCGTGCCATGACGTCATCACCGGAAGATGGAGTCCTTCCGGCACCGACCAGTCGGCC
ProSerCysHisAspValIleThrGlyArgTrpSerProSerGlyThrAspGlnSerAla

GGCCGAGTTGCGGGCTACGGCGTGATCACCAACATTATCAACGGTGGGATAGAATGCGGG
GlyArgValAlaGlyTyrGlyValIleThrAsnIleIleAsnGlyGlyIleGluCysGly

AAAGGTCAGGTTCCTCAGGTGGTGGATCGGATTGGATTCTACAAGAGGTACTGTGATATC
LysGlyGlnValProGlnValValAspArgIleGlyPheTyrLysArgTyrCysAspIle

CTTAGAGTTGGCTATGGGAACAATCTTGATTGCTATAACCAGAGGCCTTTTGGGAATGGA
LeuArgValGlyTyrGlyAsnAsnLeuAspCysTyrAsnGlnArgProPheGlyAsnGly

CTCTTGTTGGACGCCATGTAACGACTTGTCGTAGTTGTTATACATATCTGTGTTTTGAGG
LeuLeuLeuAspAlaMetEnd

GTTTGGCCGTCGTTTGTCGTCACTTCTTCGGTGACAATTTCGTTGTGTTATAGTTACTAT

ATATGTCAATGGAATAAGAACAAAGGATGTGTGCACTACAACAAAAAAAAAAAAAAAAAA

AAAAAAAAAAAAAAAAAAAAAAAAA

FIG. I pHS2 vs. refs

|    |         | 10 | 20 | 30 | 40 | 50 |
|----|---------|----|----|----|----|----|
| 14 | pHS2.tr | MRFWALTTLS | LLLSIIQGGW | AEQCGSQAGG | AVCPVGLCCS | KFGWCGSTNE |
| 21 | WIN6    | ---------- | ---------- | ---------- | ---------- | ---------- |
| 16 | pCH18   | ---------- | ---------- | -          R | L    G  N   | Q          | TD |
| 18 | TOB(A)  | ---------- | ---------- | -          R    S | | | D |

|    |         | 60 | 70 | 80 | 90 | 100 |
|----|---------|----|----|----|----|-----|
| 14 | pHS2.tr | YCGDG-CQSQ | C-GG-T---- | ---GRG-DIG | GLISSSAFND | MLKHRNDRWF |
| 21 | WIN6    | ---------- | ---------- | ---------- | ---------- | ---------- |
| 16 | pCH18   | KD-        | -   PSPAP-  T------ | LS    A      R T DQ | V          | GAC |
| 18 | TOB(A)  | PGN        | P   P PTPP  TPP  G - L | SI       M DQ  | | NAC |

|    |         | 110 | 120 | 130 | 140 | 150 |
|----|---------|-----|-----|-----|-----|-----|
| 14 | pHS2.tr | PAKGFYTYDA | FISGLSKAFP | CNLRTTGDDI | TRKREIAAFL | GQTSHETTGG |
| 21 | WIN6    | ---------- | -------E   | -DFGN      L  M | | |
| 16 | pCH18   |            | -AAA    Y  | -SFGN      TA |  | |
| 18 | TOB(A)  | QG      S  N | -NAARS   | -GFG S     TT A  | F  A | |

|    |         | 160 | 170 | 180 | 190 | 200 |
|----|---------|-----|-----|-----|-----|-----|
| 14 | pHS2.tr | WASAPRGPIT | LGGYCYNREP | KTLLLDYCSF | SPTWPCASGK | RYFGRGPIQL |
| 21 | WIN6    | PD    C  -Y | AW     LK - | -INCQP  DP | SNYQ VA    | Q  C |
| 16 | pCH18   | T     D  -Y | AW     FV - | -RNPSA    A | T QF   P Q Q Y | I |
| 18 | TOB(A)  | T     D  -Y | AW     WL - | QGSPG    TP | GQ      -  | K |

|    |         | 210 | 220 | 230 | 240 | 250 |
|----|---------|-----|-----|-----|-----|-----|
| 14 | pHS2.tr | SWNYNYGQCG | RRIGANLLNN | PDLVATDPVI | SFKTALWFWM | TPQSPKPSCH |
| 21 | WIN6    |        L   | DDLKLP   QE E | E         | I          | K |
| 16 | pCH18   |            | A     VD   K | S         | S          | A         S |
| 18 | TOB(A)  | H          | P     A VD | S         | S          | S |

|    |         | 260 | 270 | 280 | 290 | 300 |
|----|---------|-----|-----|-----|-----|-----|
| 14 | pHS2.tr | DVITGRWSPS | GTDQSAGRVA | GYGVITNIIN | GGIECG-KGQ | VPQVVERIGF |
| 21 | WIN6    | A     N T  | AA   LE    P |          | QG    P    | NAANED |
| 16 | pCH18   |       S T  | SA   VA R LP |  TV      | L     -R   | DSR QD |
| 18 | TOB(A)  |       I Q  | AG   RA N LP |  F       | L     -R  T | DSR QD |

|    |         | 310 | 320 | 330 | 340 | 350 |
|----|---------|-----|-----|-----|-----|-----|
| 14 | pHS2.tr | YKRYCDILIV | GYGNNLDCYN | QRPFGNGLLL | DTM <--- | |
| 21 | WIN6    | K     S GT | T     S    | Q          | YG  SG  LKDTM<--- | |
| 16 | pCH18   | F       L  | G          | S    T     | S FL  SDLVTSQ<-- | |
| 18 | TOB(A)  |         SL G | SPGD     | G          | S      V  <--- | |

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1225
        ( B ) TYPE: Nucleic Acid
        ( C ) STRANDEDNESS: Single
        ( D ) TOPOLOGY: Linear     ( i i ) MOLECULE TYPE: DNA     ( i i i ) HYPOTHETICAL: No     ( i v ) ANTI-SENSE: No     ( v ) FRAGMENT TYPE:

( v i ) ORIGINAL SOURCE:
        ( A ) ORGANISM: Ulmus Americana
        ( B ) STRAIN: NPS 3-487
        ( C ) INDIVIDUAL ISOLATE: N/A
        ( D ) DEVELOPMENTAL STAGE: N/A
        ( E ) HAPLOTYPE: N/A
        ( F ) TISSUE TYPE: N/A
        ( G ) CELL TYPE: N/A
        ( H ) CELL LINE: N/A
        ( I ) ORGANELLE: N/A     ( v i i ) IMMEDIATE SOURCE: N/A     ( v i i i ) POSITION IN GENOME: N/A     ( i x ) FEATURE:
        ( A ) NAME/KEY: chitinase encoding DNA
        ( B ) LOCATION:
        ( C ) IDENTIFICATION METHOD: sequencing
        ( D ) OTHER INFORMATION: DNA needed for chitinase
            in elm.

( x ) PUBLICATION INFORMATION:

( x i ) SEQUENCE DESCRIPTION: SEQ ID NO:1:

```
CGGGATTAAC  GAGATTCCCA  CTGTCCCTGT  CTACTACCCA  GCGAAACCAC  AGCCAAGGGA         60

ACGGGCTTGG  CAGAATCAGA  ACTAAACATG  AGG TTT TGG GCA TTG ACG ACA CTT TCT      120
                                   Met Arg Phe Trp Ala Leu Thr Thr Leu Ser Leu
                                                     5                      10

CTA TTG TCC ATT ATC CAA GGA GGC TGG
    GCA GAG CAA TGT GGA AGC CAA GCT GGG GGT GCA          180

Leu Leu Ser Ile Ile Gln Gly Gly Trp
```

-continued

```
                        15                          20
            Ala Glu Gln Cys Gly Ser Gln Ala Gly Gly Ala
                            25                  30

GTG TGT CCC GTT GGG CTC TGC TGC AGC
AAA TTT GGG TGG TGT GGG AGC ACA AAC GAG TAC         240
Val Cys Pro Val Gly Leu Cys Cys Ser
            35                  40
            Lys Phe Gly Trp Cys Gly Ser Thr Asn Glu Tyr
                            45                  50

TGT GGT GAT GGC TGC CAA AGC CAA TGT
GGC GGC AGC GGT AGC GAT GAC ATT GGC GGT CTC         300
Cys Gly Asp Gly Cys Gln Ser Gln Cys
            55                  60
            Gly Gly Ser Gly Ser Asp Asp Ile Gly Gly Leu
                            65                  70

ATA TCA AGC TCC GCC TTT AAT GAC ATG
CTT AAG CAT CGT AAC GAC GGT GGT TGT CCT GCC         360
Ile Ser Ser Ser Ala Phe Asn Asp Met
            75                  80
            Leu Lys His Arg Asn Asp Gly Gly Cys Pro Ala
                            85                  90

AAG GGG TTT TAC ACC TAT GAT GCT TTT
ATT GCG GCT GCC AAG GCT TTC CCT GCA TTT GGC         420
Lys Gly Phe Tyr Thr Tyr Asp Ala Phe
            95                  100
            Ile Ala Ala Ala Lys Ala Phe Pro Ala Phe Gly
                            105                 110

TCC ACC GGC GAT GAT ACC ACC CGT AAA
AGG GAG ATT GCT GCT TTC TTA GGT CAA ACT TCC         480
Ser Thr Gly Asp Asp Thr Thr Arg Lys
            115                 120
            Arg Glu Ile Ala Ala Phe Leu Gly Gln Thr Ser
                            125                 130

CAT GAA ACT ACA GGT GGG TGG GCA AGT
GCA CCC GAC GGT CCA TAC TCT TGG GGA TAC TGC         540
His Glu Thr Thr Gly Gly Trp Ala Ser
            135                 140
            Ala Pro Asp Gly Pro Tyr Ser Trp Gly Tyr Cys
                            145                 150

TAC AAT AGG GAG CAA AAC CCT TCT TCC
GAT TAT TGT TCT TTT AGT CCT ACT TGG CCT TGT         600
Tyr Asn Arg Glu Gln Asn Pro Ser Ser
            155                 160
            Asp Tyr Cys Ser Phe Ser Pro Thr Trp Pro Cys
                            165                 170

GCT TCC GGA AAG AGA TAC TTT GGC CGT
GGT CCC ATT CAA CTC TCC TGG AAC TAC AAT TAT         660
Ala Ser Gly Lys Arg Tyr Phe Gly Arg
            175                 180
```

|     | Gly | Pro | Ile | Gln | Leu | Ser | Trp | Asn | Tyr | Asn | Tyr |     |
|     |     |     |     | 185 |     |     |     |     | 190 |     |     |     |

```
GGA CAG TGT GGA AGG GCC ATA GGA GCA
    AAC CTA TTA AAC AAC CCT GAT CTC GTA GCA ACT          720
Gly Gln Cys Gly Arg Ala Ile Gly Ala
            195                 200

Asn Leu Leu Asn Asn Pro Asp Leu Val Ala Thr
                    205                 210

GAC CCT GTC ATT TCC TTC AAA ACG GCC
    TTA TGG TTC TGG ATG ACC CCA CAG TCA CCA AAG          780
Asp Pro Val Ile Ser Phe Lys Thr Ala
            215                 220

Leu Trp Phe Trp Met Thr Pro Gln Ser Pro Lys
                    225                 230

CCC TCG TGC CAT GAC GTC ATC ACC GGA
    AGA TGG AGT CCT TCC GGC ACC GAC CAG TCG GCC          840
Pro Ser Cys His Asp Val Ile Thr Gly
            235                 240

Arg Trp Ser Pro Ser Gly Thr Asp Gln Ser Ala
                    245                 250

GGC CGA GTT GCG GGC TAC GGC GTG ATC
    ACC AAC ATT ATC AAC GGT GGG ATA GAA TGC GGG          900
Gly Arg Val Ala Gly Tyr Gly Val Ile
            255                 260

Thr Asn Ile Ile Asn Gly Gly Ile Glu Cys Gly
                    265                 270

AAA GGT CAG GTT CCT CAG GTG GTG GAT
    CGG ATT GGA TTC TAC AAG AGG TAC TGT GAT ATC          960
Lys Gly Gln Val Pro Gln Val Val Asp
            275                 280

Arg Ile Gly Phe Tyr Lys Arg Tyr Cys Asp Ile
                    285                 290

CTT AGA GTT GGC TAT GGG AAC AAT CTT
    GAT TGC TAT AAC CAG AGG CCT TTT GGG AAT GCA         1020
Leu Arg Val Gly Tyr Gly Asn Asn Leu
            295                 300

Asp Cys Tyr Asn Gln Arg Pro Phe Gly Asn Gly
                    305                 310

CTC TTG TTG GAC GCC ATG TAA CGA CTT
    GTC GTA GTT GTT ATA CAT ATC TGT GTT TTG AGG         1080
Leu Leu Leu Asp Ala Met
            315

GTTTGGCCGT CGTTTGTCGT CACTTCTTCG GTGACAATTT CGTTGTGTTA TAGTTACTAT   1140
ATATGTCAAT GGAATAAGAA CAAAGGATGT GTGCACTACA ACAAAAAAAA AAAAAAAAA    1200
AAAAAAAAAA AAAAAAAAAA AAAAA                                        1225
```

CHITINASE CDNA CLONE FROM A DISEASE RESISTANT AMERICAN ELM TREE

BACKGROUND OF THE INVENTION (1) Field of the Invention

The present invention relates to a unique cDNA derived from a disease resistant hybrid Elm Tree which encodes a chitinase, a signal peptide and a sorting peptide. In particular the present invention relates to cDNA as set forth in SEQ ID NO:1.

(2) Description of Related Art

Chitinases are pathogenesis response-related proteins found in a wide variety of plants. Several lines of evidence suggest strongly that chitinases are antifungal proteins. Accumulation of chitinase (Meins, F., Ahl, P., Plant Cell 61:155–161 (1989); Métraux, J. P., et al., Physiol Mol Plant Path 28:161–169 (1986); and Rasmussen, U., et al., Planta 187:328–334 (1992)) and mRNA encoding chitinase (Roby, D., et al., Plant Sci 52:175–185 (1987); Roby, D., et al., Physiological and Molecular Plant Pathology 33:409–417 (1988); and Meins, F., et al., Plant Cell 1:447–457 (1989)) are induced strongly during the course of a fungal infection. This induction is also seen when plant tissue is treated with fungal cell wall material (Kurosaki, F., et al., Physiol Mol Plant Path 31:211–216 (1987); Roby, D., et al., Biochem Biophys Res Comm 143(3):885–892 (1987)). Ethylene, a gaseous plant hormone also produced during the course of a fungal infection, strongly induces chitinase activity (Boller, T., Oxford Surveys of Plant Molecular and Cell Biology 5:145–174 (1988); and Boller, T., et al., Planta 157:22–31 (1983)). Finally, induction also results from wounding (Parsons, T. J., et al., Proc Natl Acad Sci USA 86:7895–7899 (1989)), conditions which could mimic cell death during an active infection.

WO 90/07001 to Broglie et al describes DNA encoding chitinases for use in inhibiting fungi in detail. The techniques described in this patent application are applicable to the present invention.

In elms, pathogenesis of the fungus *Ophiostoma ulmi*, the causative agent of Dutch elm disease (DED) is well understood as is the physiological response of the elm to infection. Very little, however, is known about the molecular mechanisms of elms' disease response, and nothing of the production of pathogenesis-related (PR) proteins, such as chitinase. Little is also known about what enables some species of elm to resist *O. ulmi* infection.

SUMMARY OF THE INVENTION

It is therefore an object of the present invention to provide a novel cDNA from a DED resistant hybrid elm which encodes a chitinase protein linked to a sorting peptide sequence and a signal peptide sequence. Further, it is an object of the present invention to provide cells producing the chitinase activity. Further still, it is an object of the present invention to provide a method and compositions for the application of the peptide. These and other objects will become increasingly apparent by reference to the following description and the drawings.

BRIEF DESCRIPTION OF THE DRAWINGS

FIG. 1 is a nucleotide and deduced protein sequence of the cDNA for the elm pHS2 clone. Underlined residues in the N-terminus represent the signal peptide. Underlined residues in the C-terminal end represent the C-terminal extension. Underlined residues in the 3' untranslated region indicate putative polyadenylation signals.

FIGS. 5A and 5B are graphs.

DETAILED DESCRIPTION OF PREFERRED EMBODIMENTS

The present invention relates to a gene which encodes a polypeptide in pure form having a chitinase-like activity and a signal and a sorting peptide as set forth in SEQ ID NO:1.

Further, the present invention relates to a composition which comprises a purified protein which inhibits *Ophiostoma ulmi* and has a chitinase-like activity encoded by a gene as set forth in SEQ ID NO:1 and an agriculturally acceptable carrier, the composition containing an amount of the protein which inhibits the *Ophiostoma ulmi* upon application to a plant.

The present invention also relates to cells transformed with the gene.

Finally, the present invention relates to a method for inhibiting a fungus which comprises applying a protein having a chitinase-like activity and encoded by a gene as set forth in SEQ ID NO:1 in an inhibiting amount to the fungus.

The present invention includes transformed cells which produce the chitinase, either separately or with the sorting and signal peptides. One preferred cell is *Escherichia coli*. The DNA is introduced into the cells by known methods. The cells can be in culture to produce the chitinase or can be in the form of plants which are resistant to *Ophiostoma ulmi*, particularly elms.

The hydrolytic enzyme chitinase has been implicated in the resistance of many plants to fungal attack, primarily because it accumulates to high levels during infection or in the presence of fungal cell wall material. Although many chitinases have been described in herbaceous plants, the study of these enzymes in hardwoods has been extremely limited. The isolation and initial characterization of a 1225 bp full-length cDNA clone encoding a chitinase from a DED "resistant" selection NPS 3-487 hybrid elm Ulmus spp. was unexpected.

The cloning was based upon sequence homology using WIN6, a cDNA to a wound-induced mRNA from poplar. WIN6 was used to probe a cDNA library of 3-487 mRNA from callus tissue induced with *Ophiostoma ulmi*, the causative organism of Dutch elm disease. The predicted translation product is a 321 residue Class I chitinase (by the nomenclature of Shinshi et al., Plant Mol Biol 14:357–368 (1990)) containing the characteristic catalytic and cysteine-rich domains. A C-terminal extension, which has been shown to route proteins into the vacuole, is also present. This chitinase has 70.5% sequence identity with Class I A tobacco chitinase, 68.6% with the bean pCH18 translation product, and 67% with that from poplar WIN6. The cDNA sequence and predicted translation product, as well as several sequence analyses, are presented herein.

Example 1

A chitinase-like cDNA sequence was isolated from an *O. umli*-induced NPS 3-487 cDNA library. NPS-3- 487 is an American elm selected by the National Park Service in Washington, D.C. and was found to be moderately resistant to the DED using inoculation techniques.

Materials and Methods

Callus cultures were initiated from young leaves of greenhouse grown rooted cuttings of hybrid elm selection NPS 3-487. First and second expanded young leaves were surface sterilized in 20% CLOROX (Clorox Professional Co., Oakland, Calif.) hypochlorite and cultured in elm callus initiation medium including ½ strength modified MS medium, 40 g/L maltose, 100 mg/L casein hydrolysate, 100 mg/L thiamine, 2.5 mM 2,4 D, 1 mM kinetin, 100 ml/L coconut milk (Sigma Chemicals, St. Louis, Mo.) and 6.5 g/L Phytagar (BRL). Cultures were incubated in dark at 24°±2° C. for 3–4 weeks or until distinct calli (4–5 mm diameter) were established. Vigorously growing calli were subcultured on the same media every three to four weeks.

Three avirulent (Q311, Q412 and SSMF) and one virulent (CEF16K) strains of *O. ulmi* (described in the literature) were used for putative induction of elm callus. Fungi were grown of PDA (potato dextrose agar, Sigma Chemicals)-impregnated filter paper circles for three to four days; filters containing the pathogen were then overlaid on callus cultures for 24 hours. Fungus-treated calli were flash frozen in liquid nitrogen and stored at –80° C. until used.

A unidirectional cDNA library was custom made by Clontech (Palo Alto, Calif.) as directed by the inventors. Briefly, total RNA was isolated from equal mixtures of calli induced as above, using a guanidium-based method and poly A+ mRNA affinity purified via poly U sepharose using standard protocols (J. Sambrook, E. F. Fritch and T. Maniatis, Molecular Cloning: A Laboratory Manual, Cold Spring Harbor Laboratory Press, N.Y. (1989)). Olido dT (septadecamer) attached to an Xho I linker was used as the primer for first strand synthesis. Double stranded cDNA as linked with Eco RI adapters and the complete, end modified cDNA cloned in Eco RI/Xho I-opened bacteriophage lambda Zap II (Stratagene). The recombinant phage was plated on *E. coli* SURE (SURE strain:e14-(mcrA), Δ(mcrCB-hsdSMR-mrr) 171, endA1, supE44, thi1, gyrA96, relA1, lac, recB, recJ, sbcC, umuC: Tn5 (kan$^r$), uvrC, (F' proAB, lacI$^q$ZΔM15, Tn10(tet$^r$)) (Stratagene, San Diego, Calif.) cells and amplified one cycle.

A 764 bp wound inducible *Populus* spp (poplar) cDNA (Parsons, T. J., et al., Proc Natl Acad Sci USA 86:7895–7899 (1989)), which appears to encode a chitinase, was used as a heterologous probe at moderate stringency (3×SSPE at 60° C.) to screen the cDNA library. This yielded 0.2% primary plaques with varying signal intensities. One of the triple plaque purified phage clones was subcloned in pBS II KS using biological rescue and sequenced at the Plant Research Laboratory Sequencing Facility at Michigan State University.

Sequence analyses of the predicted protein product of pHS2 were conducted on a Macintosh IIsi (Apple Computer Co., Cupertino, Calif.) with either the DNA Strider™ (shareware version (International Biotechnologies Inc., Eastman Kodak Co., Rochester, N.Y.) or MacVector™ software packages (International Biotechnologies Inc., Eastman Kodak Co., Rochester, N.Y.). Comparisons to known chitinase sequences were performed by hand aided by Seqed for the Macintosh.

Figure 2:
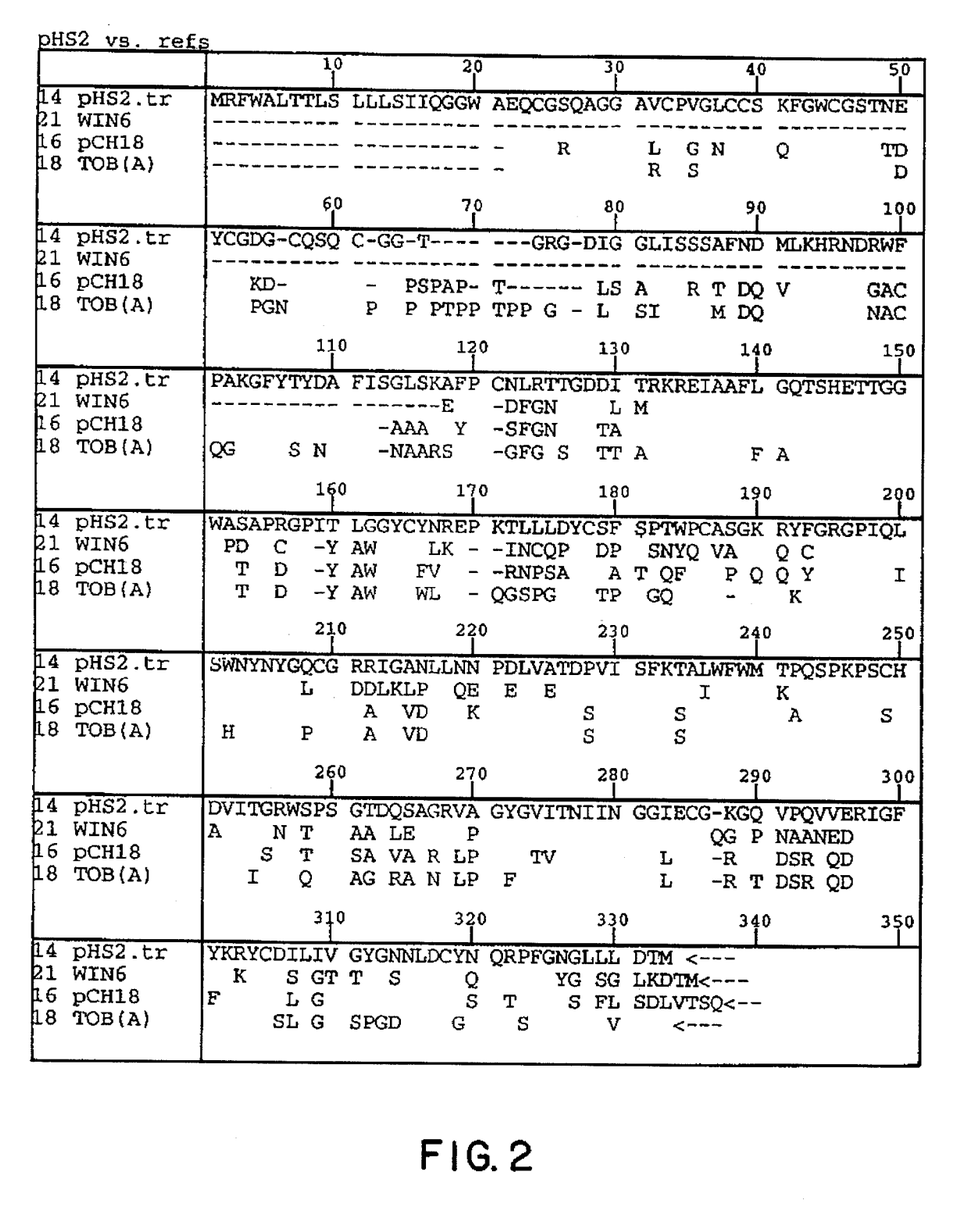
FIG. 2 is a chart showing a comparison of pHS2 predicted protein sequence to that of *Populus* WIN6 (Parsons, T. J., et al., Proc Natl Acad Sci USA 86:7895– 7899 (1989)), bean pCH18 (Broglie, et al., Proc Natl Acad Sci USA 83:6820–6824 (1986)) and tobacco CHN17 (TOB (A); (Shinshi, H., et al., Plant Mol Biol 14:357–368 (1990)) chitinases. Only residues differing from that from pHS2 are shown. Dashes to left of pCH18 and TOB (A) substitute for the signal peptide. Dashes to the left of WIN6 indicate limits of published sequence. Dashes within sequences indicate realignment for greater sequence identity. ←— indicates C-terminus of predicted protein product. Sequence alignment aided by Seqed™ for the Macintosh.

The full length cDNA clone, designated pHS2, has a 951 nucleotide open reading frame (FIG. 1). Using the 317 amino acid deduced sequence as the reading frame, a search of the PDB (protein DataBank) Swissport, PIR Genbept (cds translation from Genbank), Kabartpro (Kabartsev of Protein J. immunological interest of value, Genbank/EMBL databases using BLAST (Basic Local Alignment Search Tool) The National Center of Biotechnology Information NIH, Bethesda, Md. (Kardin, S. and Altschul, S. F., Proc. Natl. Acad. Sci. USA 87:2264–2268 (1990)) showed 50 of the 53 best matches to be chitinases; the remaining three were lectins or agglutinins, which share a chitin-binding domain with the pHS2 translation product. The predicted amino acid sequence of this 1236 bp clone, designated ECH2, revealed homology to bean, poplar, and tobacco class I chitinases (FIG. 2) strongly suggesting that this cDNA encodes a chitinase in this hybrid elm. The amino acid sequence of this chitinase-like product has 68.6% sequence identity to that of the translation product of the Phaseolus chitinase clone bean pCH18 (Broglie, et al, Proc natl Acad Sci USA 83:6820–6824 (1986)), 70.5% to the tobacco CHN17 chitinase (Shinshi, H., et al., Plant Mol Biol 14:357–368 (1990)), and 67% to poplar WIN6 (Parsons, et al., Proc Natl Acad Sci USA 86:7895–7899 (1989)) translation product (Comparisons do not consider the signal peptide sequences).

The first 21 residues of pHS2 comprise a signal peptide (FIG. 1); this peptide has the characteristic hydrophobicity coupled with a positively charged residue within three residues of the initial methionine (von Heijne, G., Eur J Biochem 133:17–21 (1983)). The C-terminal seven residues appear to comprise a second routing peptide known as a C-terminal extension. It has been established that this sequence is sufficient and necessary to direct a protein into the vacuole (Chrispeels and Raikhel, The Plant Cell 3:1–9 (1991)).

The 3' untranslated region pHS2 reveals three putative polyadenylation signals as described by Joshi (Joshi, C. P., Nucleic Acid Res. 15(23): 9627–9640 (1987)). A classic AATAAA signal is not present; however, an AATAAG and an AACAAA are present. Currently it is believed that the AATAAG is the more probable signal as this motif is present in another chitinase-like clone from this elm. Immediately 5' to the AATAAG is a YAYTG-like sequence (CAATG). Finally, ten nucleotides downstream, a TGTGTGCGCT is present which has high identity to a third olyadenylation motif (Joshi, 1987).

Analysis of Predicted Protein Product

Figure 3:
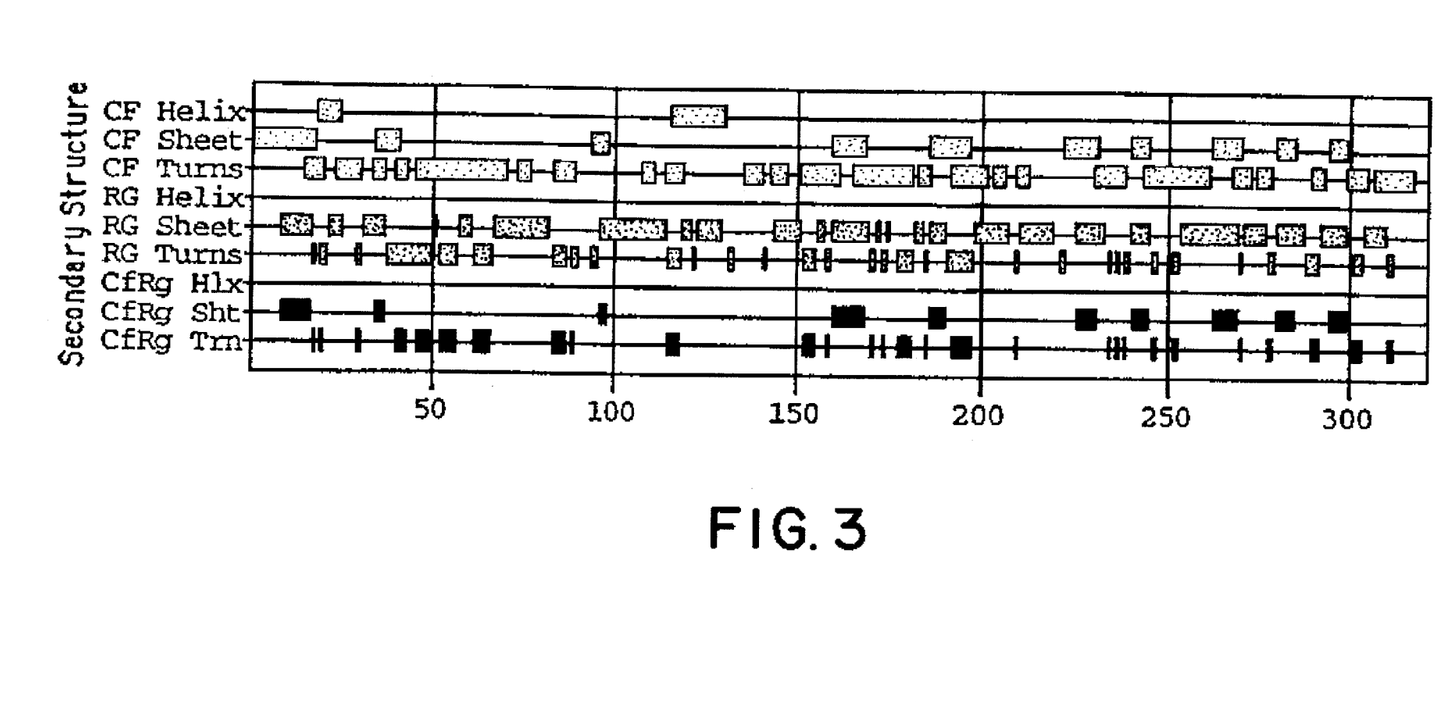
FIG. 3 is a graph showing predictions of α-helix, β-sheet, and turn-forming regions by the Chou-Fasman (CF) and Robson-Garnier (RG) algorithms. A consensus of the two methods is also calculated (CfRg Hlx, Sht, Trn). Analysis performed by MacVector™ software (International Biotechnologies, Inc., Eastman Kodak Co., Rochester, N.Y.
Figure 4A:
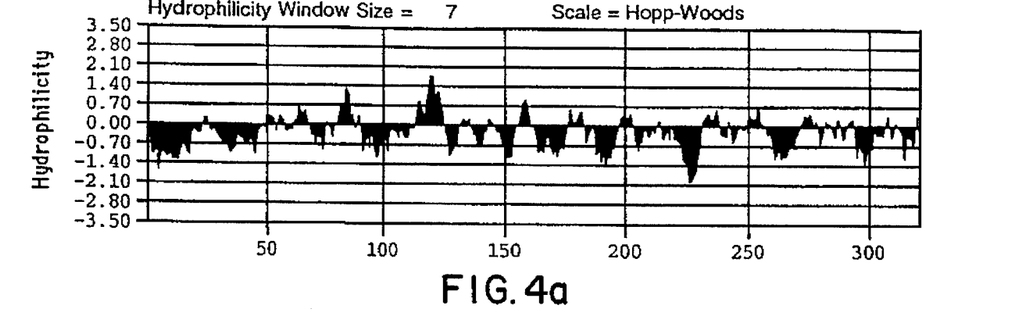
FIGS. 4A–4C are graphs showing predictions of ECH2 hydrophilicity using the Hopp-Wood, Kyle-Doolittle, and GES algorithms. Window size=7 in all cases. The analysis was performed by MacVector™ software.
Figure 4B:
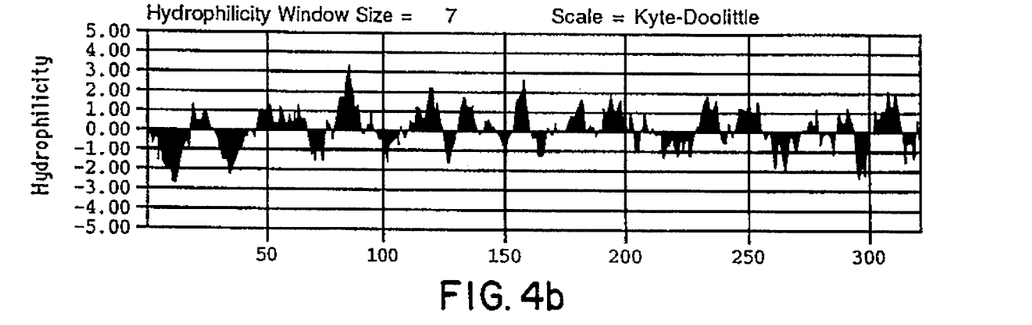
Figure 4C:
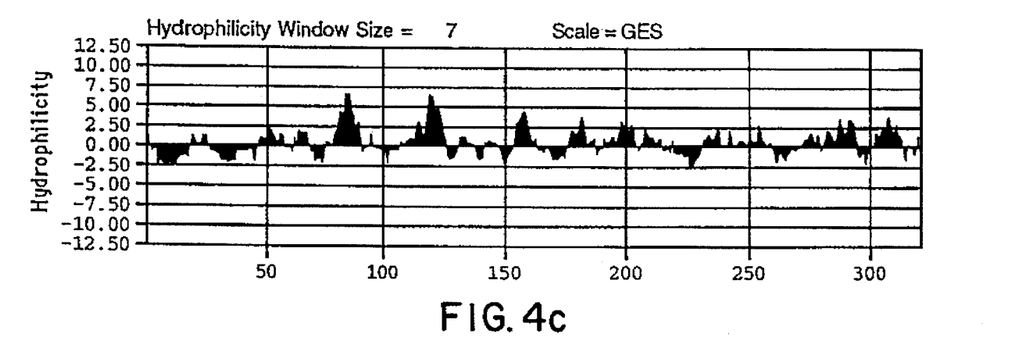
Figure 5A:
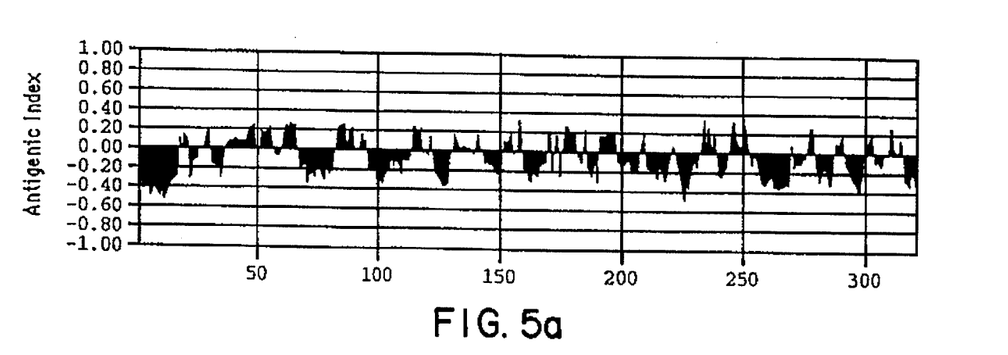
FIG. 5A shows the antigenic index of ECH2.
Figure 5B:
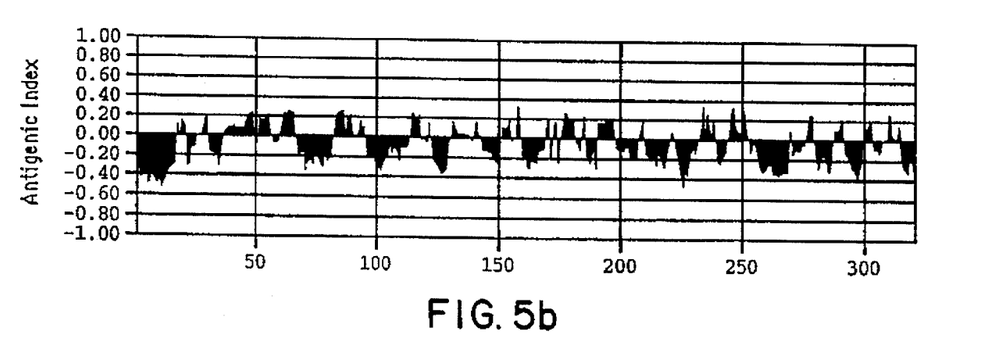
FIG. 5B shows the surface probability of ECH2. Analysis performed by MacVector™ software.

The predicted translation product of pHS2 was analyzed for surface probability, the presence of hydrophobic domains, alpha helices and beta sheets, and antigenic sites. Using a consensus of the Chou-Fasman and Robson-Garnier algorithms (FIG. 3), ECH2 contains ten regions with a high probability of forming β-sheets. No alpha helices are predicted; although three regions are predicted by the Chou-Fasman method, none are by Robson-Garnier. 28 regions which may form turns are also predicted. It should be noted that, of the two prediction algorithms, Robson-Garnier is the more stringent (yon Heijne, G., Sequence analysis in molecular biology: Treasure trove or trivial pursuit. Academic Press, Inc. San Diego (1987)). The overall hydrophilicity of ECH2 was determined by the Hopp-Woods (HW; FIG. 4A; Hopp and Woods, Proc Natl Acad Sci USA 78(6):3824–3828 (1981); Kyte-Doolittle (KD; FIG. 4B; Kyte and Doolittle, J. Mol Biol 157:105–132 (1982), and GES (FIG. 4C) algorithms. While the HW method predicts a somewhat hydrophobic protein, the KD and GES methods predict a moderately hydrophilic protein. Two regions predicted as strongly hydrophobic by all three methods include the signal peptide and the chitin-binding domain. While there are a fair number of predicted antigenic sites (FIG. 5A), there are only six major regions, plus several minor ones, predicted to comprise to the protein's surface (FIG. 5B). This is interesting in that antigenicity predictions are largely based on which residues are most likely to be exposed to the protein's surface.

Certain aspects of the present invention are described in Dutch Elm Disease Research, pages 1–5, published Aug. 9, 1994 by Springer-Verlag, New York, N.Y. It is intended that the foregoing description be only illustrative of the present invention and that the present invention be limited only to the hereinafter appended claims.

I claim:

1. An isolated gene which encodes a polypeptide in pure form having an enzyme activity which inhibits *Ophiostoma ulmi* and a signal and a sorting peptide as set forth in SEQ ID NO:1.

2. An isolated gene which encodes a polypeptide having an enzyme activity which inhibits *Ophiostoma ulmi* and a signal and a sorting peptide derived from an American Elm which is resistant to *Ophiostoma ulmi* wherein the enzyme activity is that of SEQ ID NO:1.

3. A transformed cell which expresses the gene of claim 1.

4. The cell of claim 3 which is *Escherichia coli.*

* * * * *